United States Patent [19]

Kabasakalian et al.

[11] 3,998,708
[45] Dec. 21, 1976

[54] ELECTROCHEMICAL PROCESS FOR PREPARING HYDROXYLAMINOEVERNINOMICINS

[75] Inventors: Peter Kabasakalian, Bloomfield; Sami Y. Kalliney, Parsippany; Ashit K. Ganguly, Upper Montclair; Anita Westcott, Montclair, all of N.J.

[73] Assignee: Schering Corporation, Kenilworth, N.J.

[22] Filed: Jan. 19, 1976

[21] Appl. No.: 650,082

[52] U.S. Cl. .............................. 204/59 R; 204/74; 536/17

[51] Int. Cl.$^2$ ................. C25B 3/04; C07D 325/00; C07H 15/00

[58] Field of Search .......................... 204/59 R, 74; 260/210 AB

[56] References Cited

UNITED STATES PATENTS

| | | | |
|---|---|---|---|
| 3,103,473 | 9/1963 | Juda | 204/77 |
| 3,361,653 | 1/1968 | Miller | 204/59 |
| 3,475,300 | 10/1969 | Staal | 204/74 |
| 3,505,187 | 4/1970 | Austin et al. | 204/74 |
| 3,901,973 | 8/1975 | Harris | 424/118 |
| 3,915,956 | 10/1975 | Ganguly et al. | 260/210 AB |
| 3,920,629 | 11/1975 | Garrguly et al. | 260/210 AB |

FOREIGN PATENTS OR APPLICATIONS 869,773    6/1961    United Kingdom .................. 204/74

*Primary Examiner*—F.C. Edmundson
*Attorney, Agent, or Firm*—Mary S. King

[57] ABSTRACT

Hydroxylaminoeverninomicins having antibacterial activity are prepared by electrochemically reducing the corresponding everninomicin having a nitro function or the corresponding nitrosoeverninomicin in an aqueous miscible organic solvent under an inert atmosphere or in an anhydrous aprotic solvent in the presence of carbon dioxide. Additionally, nitrosoeverninomicins, upon electrochemical reduction in an aprotic solvent under an inert atmosphere, are converted to the corresponding hydroxylaminoeverninomicins. Preferred starting compounds are everninomicins B, C and D whereby are obtained hydroxylaminoeverninomicins B, C and D, respectively. Particularly useful is the electrochemical reduction of everninomicin D in anhydrous dimethylformamide in the presence of carbon dioxide to obtain hydroxylaminoeverninomicin D of excellent purity in high yields.

16 Claims, No Drawings

2

ELECTROCHEMICAL PROCESS FOR PREPARING HYDROXYLAMINOEVERNINOMICINS

FIELD OF INVENTION

This invention relates to a novel electrochemical reduction process.

More specifically, this invention relates to the process of preparing hydroxylaminoeverninomicins having antibacterial activity by electrochemically reducing an everninomicin having a nitro function, or a nitrosoeverninomicin.

In particular, this invention relates to the process of electrochemically reducing an everninomicin selected from the group consisting of everninomicin B, everninomicin C, everninomicin D, nitroso derivatives thereof, and phenolic mono-cationic salts and N-methylglucamine salts of the foregoing, whereby are obtained the corresponding hydroxylaminoeverninomicin B, C and D, respectively.

PRIOR ART

Hydroxylaminoeverninomicins are antibacterial substances described in U.S. Pat. No. 3,915,956 of Ashit K. Ganguly and Olga Sarre for *Reduction Products of Everninomicins and Methods for their Preparation*. The process for preparing the hydroxylaminoeverninomicins described therein comprises treating an everninomicin antibiotic having a nitro function selected from the group consisting of everninomicin B, everninomicin C, and everninomicin D with aluminum amalgam in aqueous alcohol whereby is produced a product mixture having at least two antibacterial substances and comprising the corresponding hydroxylaminoeverninomicin and nitrosoeverninomicin. A preferred species of the prior art process is that wherein the starting compound is everninomicin D whereby is produced a mixture comprising hydroxylaminoeverninomicin D and nitrosoeverninomicin D, of which hydroxylaminoeverninomicin D is the preferred antibacterial agent since it has enhanced activity against gram-positive bacteria as compared with the co-produced nitrosoeverninomicin; moreover, hydroxylaminoeverninomicin D has comparable activity with that of the starting antibiotic, everninomicin D, when administered by injection as the sodium salt and, advantageously, is more rapidly absorbed, produces higher serum levels, and is more rapidly excreted than is everninomicin D.

In U.S. Pat. No. 3,901,973, an improvement of the aforedescribed process for preparing hydroxyaminoeverninomicins is described whereby the yield of hydroxylaminoeverninomicin is increased from about a 40% to 50% yield to about a 78% to a 90% yield, said improvement being the use of a different solvent, i.e. instead of aqueous alkanol, using an aprotic solvent having a dielectric constant less than 15 (preferably tetrahydrofuran) in the presence of water substantially equimolar to the everninomicin starting compound.

In the aforedescribed prior art processes for preparing hydroxylaminoeverninomicins, the aluminum reagent is costly and preferably must be prepared just prior to use. Additionally, its use entails the necessity of removing the oxidized amalgam after the process is completed. Moreover, in both the improvement and original aluminum amalgam processes, there are produced difficultly separable product mixtures necessitating careful and sometimes repeated chromatographic, extraction, and crystallization procedures in order to isolate and purify and hydroxylaminoeverninomicin product.

By our invention, hydroxylaminoeverninomicins are conveniently produced from the corresponding nitrocontaining everninomicins without the need of utilizing a costly reagent which requires preparation just before use and separation from the reaction mixture just after use. Moreover, by our invention, hydroxylaminoeverninomicins of high purity (95% or better when preparing hydroxylaminoeverninomicin D) are prepared from the corresponding nitro-containing everninomicin or nitroso derivative thereof in excellent yields (of about 80% or better in the case of hydroxylaminoeverninomicin D) and are easily isolated from the electrochemical reduction product. Our invention thus provides a convenient method of preparing hydroxylaminoeverninomicins of excellent purity in high yields.

GENERAL DESCRIPTION OF THE INVENTION

The process sought to be patented comprises electrochemically reducing an everninomicin selected from the group consisting of everninomicin B, everninomicin C, everninomicin D, nitrosoeverninomicin B, nitrosoeverninomicin C, nitrosoeverninomicin D, and phenolic monocationic salts and N-methylglucamine acid addition salts of the foregoing, at a cathode potential of about at least as negative as the lowest potential on the rising portion of the polarographic current-potential (i.e. i-E) curve of said everninomicin in a medium selected from the group consisting of an anhydrous aprotic solvent in the presence of carbon dioxide, an aqueous medium comprising a miscible organic solvent and water buffered to a pH in the range of from about 6 to about 13, usually about pH 7 (preferably 6.5 to 7.5), under an inert atmosphere, and when said everninomicin is a nitrosoeverninomicin, an aprotic solvent in an inert atmosphere, and having an electrolyte comprising a difficultly reducible cation selected from the group consisting of alkali metal, and N-alkyl-substituted ammonium ions whereby is produced the corresponding hydroxylaminoeverninomicin selected from the group consisting of hydroxylaminoeverninomicin B, hydroxylaminoeverninomicin C, and hydroxylaminoeverninomicin D.

Our process is preferentially carried out in an anhydrous aprotic solvent in the presence of carbon dioxide, since good yields (usually 80% theory or better) of purer hydroxylaminoeverninomicin are produced thereby, whereas about the same yields of less pure hydroxylaminoeverninomicin are produced when our electrochemical reduction process is carried out in an aqueous organic solvent mixture. Moreover, when utilizing an anhydrous solvent in the presence of carbon dioxide in our process, there is eliminated the necessity of using buffering agents which are essential when carrying out our process in an aqueous solvent to minimize decomposition of both the everninomicin starting compound and the hydroxylaminoeverninomicin reduction product.

When carrying out our process in an anhydrous aprotic solvent utilizing an everninomicin or salt thereof as starting compound, it is essential that carbon dioxide be present, otherwise the corresponding hydroxylaminoeverninomicin will not be produced but, rather, a mixture of everninomicin derivatives devoid of a nitro group, comprising desevernitrose derivatives and derivatives identified as everninomicins 3 and 7, which are disclosed in our co-pending application Serial No. filed on the same date as the instant application. However, when utilizing a nitrosoeverninomicin or salt thereof as starting compound, the electrochemical reduction can be carried out in an aprotic solvent with or without the presence of carbon dioxide as well as in an aqueous miscible solvent buffered to a pH in the range of from about 6 to 13, and there are produced good yields of the corresponding hydroxylaminoeverninomicin.

The preferred starting compounds for our process are everninomicin antibiotics having a nitro group, particularly everninomicin B, everninomicin C, and everninomicin D which are known antibiotics produced by the aerobic fermentation of *Micromonospora carbonacea* var. *carbonacea* and a variant thereof, *Micromonospora carbonacea* var. *aurantia* according to procedures known in the art such as described in U.S. Pat. No. 3,499,078. The isolation and purification of everninomicins B, C and D are carried out essentially as described in the art, for example, as described in U.S. Pat. No. 3,915,956.

Of antibiotics everninomicins B, C and D, everninomicin D is the most readily available and is a preferred starting compound for our electrochemical reduction process since there is produced therefrom good yields of substantially pure hydroxylaminoeverninomicin D, a valuable antibacterial agent.

The everninomicin starting compounds of our invention are compounds of the following structural formula I wherein X is nitro (i.e. X is

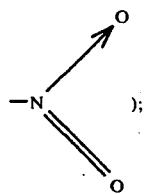

and wherein, in everninomicin B, Y is hydroxyl and Z is

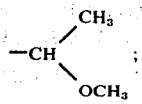

in everninomicin C, Y and Z are hydrogen; and in everninomicin D, Y is hydrogen and Z is

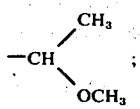

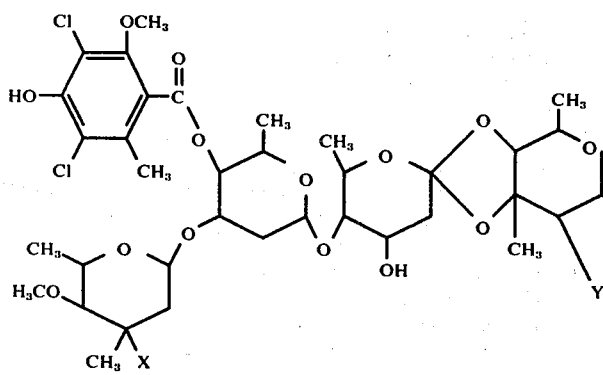

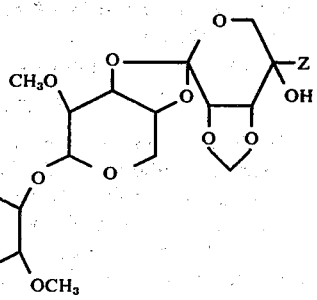

Other starting compounds of the electrochemical reduction process of this invention are nitroso derivatives of everninomicins B, C and D, i.e. nitrosoeverninomicin B, nitrosoeverninomicin C and nitrosoeverninomicin D, which are compounds of formula I wherein X is nitroso (i.e. wherein X is —N=O) with Y and Z being as defined hereinabove for the corresponding everninomicin. The nitrosoeverninomicin starting compounds of our electrochemical reduction process are antibacterials also described in U.S. Pat. No. 3,915,956. They are prepared either by the reduction of the corresponding everninomicin with aluminum amalgam in aqueous alkanol or, preferably, by oxidation of the corresponding hydroxylaminoeverninomicin utilizing reagents such as aerial oxidation in alkaline solution or with an alkali metal hypobromite (preferably sodium hypobromite) in an aprotic solvent.

The above-listed everninomicin and nitrosoeverninomicin starting compounds of our invention all contain a phenolic hydroxyl function which is readily convertible to cationic salts thereof, utilizing procedures known in the art. Such salts may also be used as starting compounds in our electrochemical reduction process provided they are soluble in the electrolysis medium, and are considered as equivalent to their free everninomicin or nitrosoeverninomicin precursors, including salts of alkali metals (e.g. sodium, potassium) and acid addition salts with amines (e.g. trialkylamines and, preferably, N-methylglucamine).

Our electrochemical reduction process consists essentially of reducing the nitro

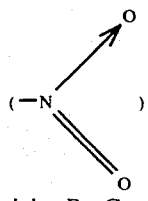

group in everninomicin B, C or D or the nitroso (—N=O) group in nitrosoeverninomicin B, C or D to a hydroxylamino (—NHOH) group in a medium selected from the group consisting of an anhydrous aprotic solvent (e.g. acetonitrile or dimethylformamide) in the presence of carbon dioxide, and an aqueous medium comprising water and a miscible organic solvent (e.g. aqueous ethanol, aqueous dimethoxyethane) buffered to a pH of from about 6 to about 13, preferably in the pH range 6.5 to 7.5, and having as an electrolyte a salt possessing a difficultly reducible cation (i.e. alkali metal and substituted ammonium ions, e.g. as in tetraalkylammonium salts such as tetrabutylammonium chloride), said electrochemical reduction being carried out at a cathode potential at least as negative as the lowest potential on the rising portion of the polarographic current-potential curve of said everninomicin starting compound, and, if desired, isolating the hydroxylaminoeverninomicin thereby produced.

One mode of our electrochemical reduction process is carried out in an aqueous medium containing an organic solvent which is miscible with water and in which the everninomicin or nitrosoeverninomicin starting compound is soluble, said aqueous medium being buffered to a pH in the range of from about 6 to about 13, usually from about 6 to about 8, preferably from about pH 6.5 to pH 7.5 .

Control of the pH of the electrolysis solution within the foregoing limits is essential when utilizing an aqueous organic solvent to insure that the hydroxylaminoeverninomicin product is obtained with a minimum of decomposition side products.

Buffering solutions which we have found useful when utilizing an aqueous organic solvent in our process include a triethylamine-triethylamine hydrochloride buffer, Clark and Lub's phosphate buffer, and malonic acid buffer, the preparation of which are described in the preparations herein. In general, any buffering agent may be used which has maximum buffering capacity in the range of pH 6 to 13, particularly in the pH 6.5 to 7.5 range, which has maximum solubility in organic solvents, and which is compatible with the catholyte.

As a general rule, when utilizing an aqueous organic solvent in our process, any organic solvent may be used which does not reduce electrolytically before the everninomicin or nitrosoeverninomicin to be reduced and which is miscible with water, and in which the starting compound and desired electrolyte is reasonably soluble. Organic solvents which may be utilized are alkanols such as ethanol, propanol and the like; glycols such as ethylene glycol and diethylene glycol; glycol ethers such as 2-ethoxyethanol; nitriles such as acetonitrile; N-substituted amides such as dimethylformamide, diethylacetamide and the like. Preferred aqueous solvents include aqueous methanol and aqueous ethanol (from about 25% to about 75% water) and aqueous 1,2-dimethoxyethane (about 50% water).

When carrying out our process in an anhydrous aprotic solvent in the presence of carbon dioxide, any anhydrous aprotic solvent may be used which does not reduce electrochemically before the everninomicin or nitrosoeverninomicin to be reduced, and in which the starting compound and desired electrolyte is reasonably soluble. Useful anhydrous aprotic solvents include nitriles such as acetonitrile; and N-substituted amides such as dimethylformamide, diethylacetamide and the like. We usually prefer to use acetonitrile or dimethylformamide.

Our novel reduction process preferentially utilizes an electrolytic cell containing a mercury or mercury amalgam cathode and an electrolyte comprising a substituted ammonium salt such as tetrabutylammonium chloride or, when an anhydrous solvent is used, an alkali metal fluoborate, particularly sodium fluoborate. Although mercury is preferred, the cathodes can be made of any conducting material possessing a high hydrogen over-voltage.

Salts which are useful as electrolytes are those possessing a difficultly reducible cation and which are sufficiently soluble in the solvent system in the electrolytic cell to give reasonably good conductance. Salts useful as electrolytes include halides of alkali metals, lithium, sodium, potassium, rubidium, and the like. However, preferred electrolytes include substituted ammonium salts (preferably tetraalkyl substituted) such as tetraethylammonium bromide, tetrabutylammonium hydroxide, triethylmonobutylammonium chloride, tetraethylammonium perchlorate, and the like, as well as mixtures thereof such as the mixture utilizing tetraethylammonium bromide and tetrabutylammonium bromide in dimethylformamide.

When carrying out our process in an anhydrous aprotic solvent (e.g. acetonitrile or dimethylformamide), particularly useful electrolytes are alkali metal fluoborates, particularly sodium fluoborate.

According to our process, an everninomicin or nitrosoeverninomicin or salt thereof may be electrochemically reduced at a negative potential at least as negative as the lowest potential on the rising portion of the current-potential ($i$-E) curve of the everninomicin, said $i$-E curve being obtained under conditions similar to those used in the reduction. The $i$-E curve of a compound may be obtained in a variety of ways such as by utilizing a recording polarograph, or by connecting a recording potentiometer across the electrolysis cell circuit and measuring the $i$-E curve under the conditions of the reduction run.

The current-potential reduction curve is known to be constant for a given compound under a given pH and a given set of conditions and, in fact, can be used as an analytical tool for identification purposes. It is also known that the $i$-E reduction curve varies with the pH, solvent and electrolyte used. It is therefore preferable for carrying out our process to determine the $i$-E curve of each everninomicin under conditions essentially identical to those to be used during the reduction itself. Thus, if everninomicin D is to be reduced in an ethanol-water (3:1) solution buffered with a triethylamine-triethylamine hydrochloride buffer utilizing an electrolytic cell having a mercury cathode, a platinum anode, and as electrolyte a tetraethylammonium halide salt, it is most desirable to have the current-potential curve determined polarographically on an aqueous ethanolic (3:1, ethanol:water) solution of everninomicin D and also having the same buffering agent and electrolyte as those to be used in the electrochemical reduction. When a polarogram or $i$-E curve for a given compound is known, one can then electrochemically reduce said compound at any potential on the rising portion of the current-voltage curve utilizing solvent, electrolyte, etc., identical to that employed when determining the polarogram ($i$-E curve).

Similarly, if everninomicin D is to be reduced in anhydrous dimethylformamide in the presence of carbon dioxide utilizing a cell having a mercury cathode, a platinum anode, and with sodium fluoborate as electrolyte, prior to reduction the current-potential curve is determined polarographically on an anhydrous dimethylformamide solution of everninomicin D in the presence of carbon dioxide and utilizing sodium fluoborate as electrolyte.

A specific $i$-E reduction curve for a compound is, in part, a measure of the range of potential at which a compound such as everninomicin D will become reduced at the cathode, which property varies at different pH values and with different solvents. The $i$-E reduction curves for compounds such as the everninomicins consist of three distinct sections and are S-shaped similar to the titration curve of a strong acid and base. The first portion (i.e. pre-reduction portion) consists of an essentially flat plateau having a constant small current value, since, without reduction of the everninomicin taking place, there is no increase in the current flowing through the cell. The beginning of the rising portion of the $i$-E curve defines the lowest potential at which the everninomicin will become reduced at the cathode. The cathode voltage at the mid-point of the rising portion of the $i$-E curve is defined as the "half-wave potential". Under a given set of conditions, the half-wave potential of the $i$-E curve varies with each compound and is a characterizing constant of the compound.

When reducing an everninomicin derivative by our novel process, it is advantageous not to use a potential more negative than the maximum potential on the rising portion of the $i$-E curve. If a more negative potential is used, competing reactions may take place such as reduction of the solvent or electrolyte. When reducing an everninomicin or nitrosoeverninomicin or salt thereof by our electrochemical process, the reduction potential usually used is in the range of from the half-wave potential to about 0.3 to 0.4 volts more negative than the half-wave potential to the $i$-E curve of the everninomicin derivative being reduced. We prefer to use a potential in the range of from the half-wave potential to about 0.3 to 0.4 volts more negative than the half-wave potential of the rising portion of the $i$-E curve of the everninomicin derivative being reduced. The potential usually used in the process of this invention is in the range of from about −1.4 to about −1.5 volts vs. a saturated calomel electrode (SCE) when the medium is an aqueous organic solvent and is at about −1.75 to about −1.85 volts vs. SCE when the medium is an anhydrous aprotic solvent in the presence of carbon dioxide.

It is evident from the foregoing, that there are countless variations of electrolytic cells which may be used when electrolytically reducing an everninomicin. Cells which are particularly useful for reducing the everninomicins are those having a three-electrode system with a saturated calomel reference electrode as well as a cathode and anode, wherein the anode and anolyte are separated from the cathode and catholyte by a porous Alundum cup, and which have a mercury cathode, a graphite anode, and an electrolyte which is preferably sodium fluoborate when utilizing an anhydrous aprotic solvent or, when utilizing an aqueous organic solvent, an electrolyte consisting of the buffer optionally combined with a tetraalkylammonium halide. Thus, for example, the reduction of an everninomicin such as everninomicin D may be effected by adding the everninomicin (e.g. about 9 gms. everninomicin D) to aqueous ethanol (e.g. 1:3) buffered to pH 6.5 with triethylamine-triethylamine hydrochloride which has been electrolyzed in a three electrode system cell such as described hereinabove at a cathode potential of about −1.4 volts until the current levels off. The electrolysis of the everninomicin D solution is continued at a cathode potential of −1.4 volts maintained by means of an automatic potentiostat, this voltage being more negative than, or equal to, the half-wave potential of everninomicin D as obtained by known polarographic techniques. When the reduction is complete as evidenced by the drop in current to a constant value, the reductive electrolysis is stopped and the reduced product (e.g. hydroxylaminoeverninomicin D) is isolated, usually by evaporating the solvent mixture in vacuo, extracting the resultant residue with a chlorinated hydrocarbon solvent (e.g. chloroform) which, in turn, is concentrated to a residue comprising the hydroxylaminoeverninomicin product (which can be further purified utilizing chromatographic techniques) in high yields (e.g. about 80% theory) of excellent purity (about 87% when electrochemically reduced in an aqueous solvent) as determined by titration as an acid (in view of the phenolic function) and as a base (in view of the hydroxylamine function), and by oxidation using potassium ferricyanide, then back titrating to determine the amount of oxidant used (another measure of the quantity of hydroxylamino function present).

Preferably, reduction of an everninomicin to produce the corresponding hydroxylaminoeverninomicin is effected in a similar three electrode system cell by dissolving the everninomicin (e.g. everninomicin D) in an anhydrous aprotic solvent containing an electrolyte (e.g. 0.01 molar sodium fluoborate in anhydrous dimethylformamide) and placing the solution in the catholyte compartment; also placing a solution of the same electrolyte in the same anhydrous solvent (e.g. 0.1 molar sodium fluoborate in anhydrous dimethylformamide) in the anolyte compartment, then bubbling anhydrous carbon dioxide through both the anolyte and catholyte solutions (e.g. for about an hour) prior to carrying out the electrolysis; while continuing to bubble carbon dioxide through the electrolyte, carry out the electrolysis at about −1.8 volts vs. SCE until the reduction is complete as evidenced by the drop in current to a constant value as determined polarographically. The reduced product (e.g. hydroxylaminoeverninomicin D) produced in high yields (i.e. from about 95% to theoretical yield) is then isolated and purified as described hereinabove.

In similar fashion, other everninomicin derivatives, i.e. everninomicin B, everninomicin C, nitrosoeverninomicin B, nitrosoeverninomicin C, nitrosoeverninomicin D, and salts thereof (e.g. the sodium salts and the N-methylglucamine salts of the foregoing) upon electrochemical reduction in aqueous ethanol buffered to pH 6.5 with triethylamine-triethylamine hydrochloride at a cathode potential of about −1.4 volts until the current drops to a constant value or, preferably, upon electrochemical reduction in anhydrous dimethylformamide in the presence of carbon dioxide at a cathode potential of about −1.8 volts until the current drops to a constant value, are converted to the corresponding hydroxylaminoeverninomicin which is isolatable via known techniques similar to those described hereinabove for hydroxylaminoeverninomicin D.

The following examples are illustrative of the best mode for carrying out our invention and are not to be construed as limiting the scope thereof, the scope of our invention, as defined by the appended claims, also including obvious equivalents suggested by our disclosure to those skilled in the art.

PREPARATION 1

Preparation of Buffer Solutions

A. Triethylamine (0.25 M)-triethylamine Hydrochloride (0.25 M) Buffer

In a liter volumetric flask, add 72 ml. of triethylamine and 250 ml. of hydrochloride acid (1.00 M). Add ethanol (or methanol) until the total volume is 1 liter.

B. Clark and Lub's Phosphate Buffer

Add 2 molar aqueous sodium hydroxide to 0.2 M aqueous potassium dihydrogen phosphate to obtain a solution of pH 7.

C. Malonic Acid Buffer

In a liter volumetric flask, add 0.05 moles malonic acid buffer, 0.09 moles sodium hydroxide and 0.1 moles tetramethylammonium chloride, then add water until the total volume is one liter. (When added to aqueous 50% ethanol or aqueous 50% methanol, the pH is about 7 at 25° C.)

EXAMPLE 1

Determination of Current-Voltage Curves and General Electrolysis Procedure Utilizing Aqueous Miscible Organic Solvent The current-potential curves of the everninomicins or nitrosoeverninomicins or salts thereof are obtained on 5 ml. portions of approximately millimolar solutions of said everninomicins or derivatives thereof utilizing a Leeds and Northrup recording polarograph (Electrochemograph Type E).

The solutions to be polarographed are prepared by dissolving in a 10 ml. volumetric flask 6 micromoles (approximately 10 mg.) of the everninomicin starting compound in about 5 ml. of methanol or ethanol, then add 0.5 ml. of 1 M aqueous tetrabutylammonium chloride, and finally add a buffer solution usually 0.05 molar in water to make a total solution volume of 10 ml.

The current-potential curves of the everninomicin B, C and D starting compounds and salts thereof in the Examples are all similar under a given set of conditions and are pH dependent, e.g. at pH 6 the half-wave potential is about −0.85 volts vs. normal calomel electrode, while at pH 7.2, the half-wave potential is about −0.89 volts vs. normal calomel electrode.

The electrolysis cell is a three-electrode system cell consisting of a cylindrical glass cathode compartment with a 1 cm. deep pool of mercury acting as cathode. Contact with the mercury is made through a side arm attached to the cell at a point below the mercury level. The anode compartment is an Alundum cup suspended in the cathode compartment with a graphite anode. The third electrode is a standard saturated calomel electrode, which is inserted in the cathode compartment with the tip just touching the mercury surface. The electrolysis is carried out, preferentially, using an automatic potentiostat such as the Lingane Jones type (J. J. Lingane et al. Anal. Chem., 22, (1169-1950), although manual potentiostats may also be used, the electrolytic reduction being carried out until the current measurement decreases to a constant value.

The anolyte and catholyte solutions are usually the same and are prepared by combining a certain volume of aqueous miscible organic solvent, e.g. 600 ml. of ethanol with aqueous buffer, e.g. 400 ml. of 0.05 molar phosphate buffer at pH 7. Part of the solution to be used in the electrolysis is added to a porous Alundum cup and allowed to stand in air until the cup becomes damp on the outside. The remaining solution is added to the electrolysis cell containing the mercury, which is cooled with an ice bath. Nitrogen is bubbled through the catholyte solution for 30 minutes, after which the Alundum cup with its graphite anode and containing the anolyte is suspended in the cathode compartment so that the bottom of the cup is near, but not touching, the mercury. A saturated calomel electrode is inserted in the cathode compartment so that the tip just touches the mercury surface. The catholyte solution is stirred and the control potential of the mercury vs. the calomel electrode is set at −1.4 volts (S.C.E.) by adjusting the potentiostat. The catholyte solution is then electrolyzed at −1.4 volts until the current approaches a constant value.

To carry out the electrochemical reduction process of this invention, the everninomicin starting compound to be reduced (e.g. everninomicin D) is now added to the catholyte solution and the electrolysis is continued until the current returns to the constant value possessed by the catholyte prior to the addition of the everninomicin. The electrolysis is usually completed in from 2 to 3 hours.

To isolate the hydroxylaminoeverninomicin thereby produced, the catholyte solution is siphoned from the mercury cathode, the cathode is washed three times with the aqueous solvent used in the catholyte solution (e.g. 95% ethanol) and the washings are combined with the original solution. After filtering the solution through Celite, the filtrate is evaporated in vacuo at room temperature and the resultant solid is extracted with a halogenated hydrocarbon such as chloroform. The chloroform solution is then evaporated in vacuo and the resultant solid chromatographed utilizing known techniques, the hydroxylaminoeverninomicin being isolated and purified as described hereinbelow.

EXAMPLE 2

Reduction of Everninomicin D in Aqueous Ethanol With Triethylamine-Triethylamine Hydrochloride Buffer Add as anolyte and catholyte to the three-electrode cell, 250 ml. of aqueous ethanol (1:3) buffered to pH 8 with 0.2 molar triethylamine-triethylamine hydrochloride. Cool the cell with an ice bath, then electrolyze the solution at a cathode potential of −1.40 volts vs. (SCE) until the current approaches a constant value. Add 9.3 g. of everninomicin D to the cell and continue electrolysis at −1.4 volts. Continue the electrolysis at a cathode potential of −1.40 volts until the current falls to a constant value.

Siphon the solution from the cell, then evaporate the solution in vacuo at room temperature; extract the solid with chloroform, then evaporate the chloroform solution to a residue comprising 9.3 g. of hydroxylaminoeverninomicin D. Purify a 200 mg. sample of the residue by chromatographing on a preparative Analtech plate (2000 m$\mu$), using a benzene:acetone (1:1) system. Elute the major band with acetone and evaporate the acetone solution to a residue comprising hydroxylaminoeverninomicin D, having an $R_f$ value of 0.31; yield = 160 mg. (80% theoretical quantity); purity about 87% as determined by titration as an acid and base, and by oxidation using potassium ferricyanide and back-titrating to determine the amount of oxidant used.

The above electrolytic reduction of everninomicin D may also be carried out in aqueous methanol (1:3), and there is obtained hydroxylaminoeverninomicin D in high yields.

EXAMPLE 3

Electrochemical Reduction of Everninomicin D in Aqueous 1,2-Dimethoxyethane (1:1) with Phosphate Buffer To 2 ml. of 1,2-dimethoxyethane add 2 ml. of 0.05 molar phosphate buffer, the resultant solution pH being at about 7.

In a manner similar to that described in Example 2, electrolyze the solution at a cathode potential of about −1.4 volts until the current approaches a constant value, then dissolve 30 mg. of everninomicin D in the electrolyzed dimethoxyethane buffered solution, electrolyze the solution containing everninomicin D at a cathode potential held at about −1.5 volts SCE in a manner similar to that described in Example 2 until the current falls to a constant value. Isolate and purify the hydroxylaminoeverninomicin D thereby obtained in a manner similar to that described in Example 2.

EXAMPLE 4

Electrochemical Reduction of Everninomicin C in Aqueous Methanol With Triethylamine-Triethylamine Hydrochloride Buffer To 3 ml. of methanol add 1 ml. of 0.2 molar triethylamine-triethylamine hydrochloride buffer, the resulting solution being at about pH 8. Electrolyze this buffered solvent at −1.4 volts until the current approaches a constant value in a three-electrode cell in a manner similar to that described in Example 2.

Dissolve 100 mg. of everninomicin C in the electrolyzed, buffered aqueous methanol and electrochemically reduce the everninomicin C in a manner similar to that described in Example 2.

In a manner similar to that described in Example 2, evaporate the electrolyzed solution to a residue, extract the residue with chloroform, evaporate the chloroform solution to a residue, then purify this residue via chromatography on preparative plates, using a benzene:acetone (1:1) system. Elute the major band with acetone and evaporate the acetone solution to a residue comprising hydroxylaminoeverninomicin C.

EXAMPLE 5

Electrochemical Reduction of Everninomicin C in Aqueous Methanol (2:3) With Malonic Acid Buffer To 6 ml. of methanol add 4 ml. of aqueous 0.05 molar malonic acid buffer, the resulting solution being at a pH of about 7. In a manner similar to that described in Example 2, electrolyze the buffered aqueous methanol in a three-electrode cell having a capacity of 25 ml. at −1.4 volts until the current approaches a constant value, then add 110 mg. of everninomicin C and electrolyze the solution at −1.4 volts in a manner similar to that described in Example 2 until the current drops to a constant value. Evaporate the solution in vacuo to a residue, extract the residue with chloroform, evaporate the chloroform solution to a residue, purify the chloroform solution residue via thin layer chromatography utilizing benzene:acetone (1:1) in a manner similar to that described in Example 2 to obtain hydroxylaminoeverninomicin C.

EXAMPLE 6

Electrochemical Reduction of Everninomicin B in Aqueous Methanol with Phosphate Buffer To 10 ml. of methanol, add 9 ml. of 0.05M aqueous phosphate buffer (pH of solution, 7). In a manner similar to that described in Example 2, add the buffered methanol solution to a three-electrode cell, electrolyze at −1.4 volts until the current approaches a constant value, then add 100 mg. of everninomicin B and continue electrolyzing the solution at −1.45 volts in a manner similar to that described in Example 2 until the current drops to a constant value.

In a manner similar to that described in Example 2, siphon the electrolyzed solution, then evaporate in vacuo at temperatures below 37° C. Dissolve the resultant residue in acetone, filter the solution through a layer of anhydrous sodium sulphate, concentrate the filtered acetone solution to a residue, then purify the residue via thin layer chromatography in a manner similar to that described in Example 2 utilizing 2000 micron Analtech Plates developed in an acetone:benzene system (7:3). Elute the major band with acetone and evaporate the acetone solution in vacuo to a residue comprising hydroxylaminoeverninomicin B; Yield = 57 mg.

EXAMPLE 7

Electrochemical Reduction of Everninomicin D in Anhydrous Dimethylformamide in the Presence of Carbon Dioxide A. Determination of Current-Potential Curve In a manner similar to that described in Example 1, the current-potential curves of the everninomicins or nitrosoeverninomicins or salts thereof are obtained utilizing a Leeds and Northrup recording polarograph (Electrochemograph type E) on solutions of said everninomicins or derivatives thereof in the same solvent and concentration and under the same conditions to be used in the electrochemical reduction.

The current-potential curves of the nitro group in the everninomicin B, C and D starting compounds and salts thereof are all similar under a given set of conditions, for example, everninomicin D in anhydrous dimethylformamide through which carbon dioxide is being bubbled yields a polarographic wave having a half-wave potential of −1.72 volts (vs. SCE).

B. Electrochemical Reduction

Prepare a solution of 10 gm. of everninomicin D in 1 liter of a 0.01 molar solution of sodium fluoborate in anhydrous dimethylformamide and place the solution in the cathode compartment of the three-electrode cell.

To the anode compartment and 1.0 molar sodium fluoborate in anhydrous dimethylformamide until the level of the anolyte solution is at least equal to the level of the catholyte solution. Bubble carbon dioxide through both the catholyte and anolyte at room temperature for about 1 hour, then electrolyze the solution at room temperature at a cathode potential of −1.8 volts (vs. SCE) until the current falls to a constant small value.

Evaporate the catholyte in vacuo at 40° C, then further dry the resultant residue in vacuo at room temperature. Dissolve the resultant residue in 600 ml. of methylene chloride and 140 ml. of a buffer at pH 5. Separate the aqueous layer, wash the methylene chloride solution twice with 100 ml. of water adjusted to pH 5 with hydrochloric acid, then wash the methylene chloride layer with saturated aqueous sodium chloride solution. Dry the methylene chloride over sodium sulfate, evaporate in vacuo, dissolve the resultant residue in 30 ml. of methylene chloride and add dropwise to 1400 ml. of hexane. Separate the resultant crystalline precipitate by filtration, wash the filtrate with hexane and dry in vacuo to obtain hydroxylaminoeverninomicin D, yield 7.8 gm. (78% theory) of about 95% purity as determined by titration as an acid and as a base and by oxidation by potassium ferricyanide and back-titrating to determine the amount of oxidizing reagent.

EXAMPLE 8

Electrochemical Reduction of Everninomicin D Tetraethylammonium Salt in Anhydrous Dimethylformamide in the Presence of Carbon Dioxide A. Catholyte Containing Potassium Iodide Prepare a solution of 1 gm. of everninomicin D tetraethylammonium salt in 100 ml. of a 0.01 molar solution of potassium iodide in anhydrous dimethylformamide. Place the solution in the cathode compartment, then add a 0.1 molar solution of tetraethylammonium fluoborate in anhydrous dimethylformamide to the anode compartment until the level of the anolyte is at least equal to the level of catholyte. Bubble carbon dioxide through both the catholyte and anolyte for an hour, then electrolyze the solution at a cathode potential of about −1.8 volts (vs. SCE) bubbling carbon dioxide through the solution until the current approaches a constant small value. Isolate and purify the resultant product in a manner similar to that described in Example 7 to obtain hydroxylaminoeverninomicin D in approximately quantitative yields.

B. Catholyte Containing Lithium Fluoborate

Prepare a solution of 100 mg. of everninomicin D tetraethylammonium salt in 100 ml. of a 0.01 molar solution of lithium fluoborate in anhydrous dimethylformamide. Place the solution in the cathode compartment, then add a 0.1 molar solution of lithium fluoborate in anhydrous dimethylformamide to the anode compartment until the level of the anolyte is at least equal to the level of the catholyte solution. Bubble carbon dioxide through both the anolyte and catholyte for at least an hour, then electrolyze the solution at a cathode potential of about −1.8 volts (vs. SCE) until the current approaches a constant small value. In a manner similar to that described in Example 7, isolate and purify the resultant product to obtain hydroxylaminoeverninomicin D in high yield of over 95% purity.

In the above procedure, by using lithium chloride instead of lithium fluoborate, there is also obtained quantitative yields of hydroxylaminoeverninomicin D.

C. Catholyte Containing Tetraethylammonium Chloride

To the cathode compartment add 100 mg. of everninomicin D tetraethylammonium salt dissolved in 100 ml. of 0.01 molar solution of tetraethylammonium chloride in anhydrous dimethylformamide. Add a 0.1 molar solution of tetraethylammonium chloride in anhydrous dimethylformamide in the anode compartment until the solution level is at least equal to that of the catholyte. In a manner similar to that described in Example 7, electrolyze a solution at a cathode potential of about −1.8 volts (vs. SCE) until the current drops to a constant small value. Isolate and purify the resultant product in a manner similar to that described in Example 7 to obtain hydroxylaminoeverninomicin D in quantitative yields.

In the procedures of Examples 7 and 8 substitute for the tetraethylammonium chloride in the anolyte and catholyte other tetraethylammonium salts, e.g. tetraethylammonium perchlorate, tetraethylammonium iodide, and tetraethylammonium bromide, and there will be obtained approximately quantitative yields of hydroxylaminoeverninomicin D.

EXAMPLE 9

Electrochemical Reduction of Nitrosoeverninomicin D in Anhydrous Dimethylformamide under an Atmosphere of Argon To the cathode compartment add 99.5 mg. of nitrosoeverninomicin D dissolved in 100 ml. of a 0.01 molar solution of sodium fluoborate in dimethylformamide, then add an 0.01 molar solution of sodium fluoborate in anhydrous dimethylformamide in the anode compartment until the solution level is at least equal to that of the catholyte. Electrolyze the solution at a cathode potential of −1.8 volts (vs. SCE) until the current drops to a constant small value. Isolate and purify the resultant product in a manner similar to that described in Example 7 to obtain hydroxylaminoeverninomicin D.

We claim:

1. The process which comprises electrochemically reducing an everninomicin selected from the group consisting of everninomicin B, everninomicin C, everninomicin D, nitrosoeverninomicin B, nitrosoeverninomicin C, nitrosoeverninomicin D, and phenolic mono-cationic salts and amine acid addition salts of the foregoing, at a cathode potential of about at least as negative as the lowest potential on the rising portion of the polarographic current-voltage curve of said everninomicin, in a medium selected from the group consisting of an anhydrous aprotic solvent in the presence of carbon dioxide, an aqueous medium comprising water and a miscible organic solvent buffered to a pH in the range of from about 6 to about 13 under an inert atmosphere and, when said everninomicin is a nitrosoeverninomicin, an aprotic solvent under an inert atmosphere, and having an electrolyte comprising a difficultly reducible cation selected from the group consisting of alkali metal and alkyl substituted ammonium ions, whereby is produced the corresponding hydroxylaminoeverninomicin selected from the group consisting of hydroxylaminoeverninomicin B, hydroxylaminoeverninomicin C, and hydroxylaminoeverninomicin D.

2. The process of claim 1 wherein said everninomicin is everninomicin D.

3. The process of claim 1 wherein said cathode potential is at least as negative as the lowest potential on the rising portion of the polarographic current-voltage curve of said everninomicin and less than the potential at which the hydronium ion or the electrolyte is reduced.

4. The process of claim 1 wherein said everninomicin is everninomicin D; said cathode is mercury at a potential of from about −1.4 volts to about −1.8 volts vs. SCE.

5. The process of claim 1 wherein said medium comprises water and a miscible organic solvent buffered to a pH in the range from about 6.5 to 7.5.

6. The process of claim 1 wherein said everninomicin is everninomicin D, said cathode is mercury at a potential of about −1.4 volts vs. SCE, and said medium is an aqueous lower alkanol buffered to about pH 7.

7. The process of claim 1 wherein said everninomicin is everninomicin D, said cathode is mercury at a potential of about −1.5 volts vs. SCE, and said medium is aqueous dimethoxyethane buffered to about pH 7.

8. The process of claim 1 wherein said everninomicin is everninomicin C, said cathode is mercury at a potential of about −1.4 volts vs. SCE, and said medium is a lower alkanol buffered to about pH 7.

9. The process of claim 1 wherein said everninomicin is everninomicin B, said cathode is mercury at a potential of about −1.4 volts vs. SCE, and said medium is aqueous methanol buffered to about pH 7.

10. The process of claim 1 wherein said medium is an anhydrous aprotic solvent in the presence of carbon dioxide.

11. The process of claim 10 wherein said aprotic solvent is dimethylformamide or acetonitrile.

12. The process of claim 1 wherein said everninomicin is everninomicin D, said cathode is mercury at a potential of about −1.8 volts vs. SCE, and said medium is anhydrous dimethylformamide in the presence of carbon dioxide.

13. The process of claim 12 when said electrolyte is sodium fluoborate.

14. The process of claim 1 wherein said everninomicin is everninomicin D tetraethylammonium salts, said cathode is mercury at a potential of about −1.8 volts vs. SCE, and said medium is anhydrous dimethylformamide in the presence of carbon dioxide.

15. The process of claim 14 wherein said electrolyte is lithium fluoborate.

16. The process of claim 14 wherein said electrolyte is tetraethylammonium chloride.

* * * * *